United States Patent [19]

Holm

[11] 4,090,863

[45] May 23, 1978

[54] COMPOSITIONS CONTAINING 5-CHLORO-3-METHYL-4-NITRO-1H-PYRAZOLE AS FRUIT ABSCISSION AGENTS

[75] Inventor: Robert E. Holm, Painesville, Ohio

[73] Assignee: Diamond Shamrock Corporation, Cleveland, Ohio

[21] Appl. No.: 603,290

[22] Filed: Aug. 11, 1975

[51] Int. Cl.² .......................... A01N 9/22; A01N 9/20
[52] U.S. Cl. ........................................ 71/92; 71/105; 71/90; 71/95; 71/97
[58] Field of Search .................................... 71/105, 92

[56] References Cited

U.S. PATENT DOCUMENTS

| | | | |
|---|---|---|---|
| 3,869,274 | 3/1975 | Corvetti et al. | 71/92 |
| 3,970,443 | 7/1976 | Holm et al. | 71/94 |

*Primary Examiner*—Catherine L. Mills
*Attorney, Agent, or Firm*—Timothy E. Tinkler; Stuart L. Melton

[57] ABSTRACT

A combination of 5-chloro-3-methyl-4-nitro-1H-pyrazole and certain imides, carbamates, or a phthalonitrile is a synergistic composition capable of promoting fruit, especially citrus fruit, abscission when applied to trees bearing same.

5 Claims, No Drawings

COMPOSITIONS CONTAINING 5-CHLORO-3-METHYL-4-NITRO-1H-PYRAZOLE AS FRUIT ABSCISSION AGENTS

BACKGROUND OF THE INVENTION

The desirability of facilitating the harvest of various agricultural crops, especially fruit crops such as citrus fruits, is readily apparent. A number of chemical compounds capable of promoting fruit abscission has been proposed, which compounds serve to reduce the pull force necessary to remove mature fruit from the tree or plant, thus rendering mechanical harvesting practical. Few of these compounds, however, have found practical utility, mainly owing to their tendency to injure immature fruit and cause blossom drop and/or their simultaneous defoliant effect.

One compound suggested for use as a citrus fruit abscission agent is 5-chloro-3-methyl-4-nitro-1H-pyrazole, i.e.,

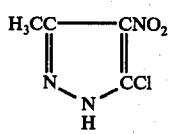

This compound and its use are described more fully in U.S. Pat. No. 3,869,274. While the compound is indeed effective in reducing the pull force necessary to remove citrus fruit from trees, its use in concentrations effective to cause abscission often results in excessive damage to the mature fruit being harvested, leading to post harvest disease and/or "off" taste in fruit juices made therefrom.

STATEMENT OF THE INVENTION

Therefore, it is an object of the present invention to provide compositions and a method of using same which are effective for promoting abscission of mature fruit, while reducing undesirable side effects.

It is a further object of the present invention to increase the ability of 5-chloro-3-4-nitro-1H-pyrazole to promote fruit abscission.

These and other objects of the present invention will become apparent to those skilled in the art from the specification and claims that follow.

There has now been found a composition capable of promoting fruit abscission, which composition consists essentially of 5-chloro-3-methyl-4-nitro-1H-pyrazole and a compound from the group N-[(trichloromethyl)thio] phthalimide, N-[(trichloromethyl)thio]-4-cyclohexene-1,2-dicarboximide, cis-N-[(1,1,2,2-tetrachloroethyl)thio]-4-cyclohexene-1,2-dicarboximide, ferric dimethyldithiocarbamate, ethylenebisdithiocarbamate manganese, ethylene bisdithiocarbamate zinc, methyl-1-(butylcarbamoyl)-2-benzimidazolecarbamate, or tetrachloroisophthalonitrile. Such a composition is effectively employed in the harvest of mature fruit by applying an abscission-promoting amount of same to the fruit locus and, subsequently, exerting sufficient force on said fruit to remove same from the tree.

DESCRIPTION OF THE PREFERRED EMBODIMENTS

Throughout the specification and claims, the term "fruit" is used to define a variety of agricultural products, the removal of which from the parent plant or tree (hereinafter, tree) may be promoted by the use of an abscission agent. Typically included are oranges, lemons, grapefruit, limes, olives, cherries, apples, pecans, and walnuts. Especially important, and referred particularly hereinafter, are the citrus fruits.

It has been theorized and substantially demonstrated that one abscission mechanism involves the increased production of ethylene within the fruit, which triggers the abscission process. 5-Chloro-3-methyl-4-nitro-1H-pyrazole is one compound which, when applied externally to mature fruit, increases internal ethylene production and, shortly thereafter, reduces the pull force necessary to remove the fruit. A direct correlation has been confirmed between the ability of a compound or composition to stimulate internal fruit ethylene production and its ability to facilitate fruit abscission.

The present invention makes use of the ability of certain imides, carbamates, and a phthalonitrile to increase this internal ethylene production, i.e., the amount of ethylene produced per a given quantity of 5-chloro-3-methyl-4-nitro-1H-pyrazole is significantly increased. A reduction in the pull force necessary to cause abscission follows. This is thought to be surprising since none of the additives alone act to produce any significant quantities of ethylene in fruit when externally applied. Thus, the invention allows the use of a lesser quantity of 5-chloro-3-methyl-4-nitro-1H-pyrazole, thereby reducing injury to the tree and any blooms and immature fruit, or causes an increased abscission-promoting effect at the same pyrazole concentration. While higher amounts have been recommended when applying the abscission agent alone, the present invention demonstrates commercially acceptable results at 5-chloro-3-methyl-4-nitro-1H-pyrazole concentrations in the applied formulation within the range of from 25 to 300, especially 50 to 250, parts per million.

The compounds effective in combination with said pyrazole according to the present invention are as follows:

N-[(trichloromethyl)thio] phthalimide:

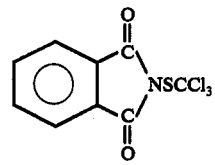

cis-N-[(trichloromethyl)thio]-4-cyclohexene 1,2-dicarboximide:

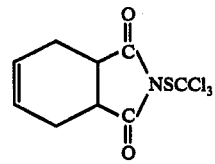

cis-N-[(1,1,2,2-tetrachloroethyl)thio]-4-cyclohexene-1,2-dicarboximide:

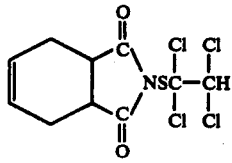

ferric dimethyldithiocarbamate:

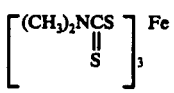

ethylenebisdithiocarbamate manganese:

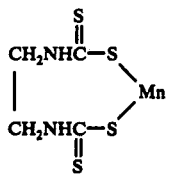

ethylenebisdithiocarbamate zinc:

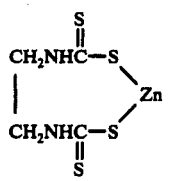

methyl-1-(butylcarbamoyl)-2-benzimidazolecarbamate:

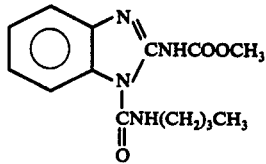

tetrachloroisophthalonitrile:

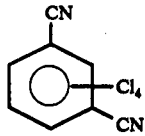

They may be employed at concentrations ranging between 50 and 1000 ppm. The ratio of the compound to the pyrazole is within the range of from 1 to 20:1, preferably 1 to 5:1, by weight.

The composition will generally be applied as an aqueous spray, this being most convenient and economical, although dusting or other methods of application are possible. Preparation of the aqueous formulation merely requires the dispersion or emulsification of the materials at the stated concentration ranges employing a non-phytotoxic surfactant, such as polyoxyethylated sorbitan monolaurate.

Thus, when the fruit has reached substantial maturity, the abscission-promoting composition is applied, generally 3 to 10 days prior to the desired harvesting date, by spraying the fruit locus, although the entire tree may be treated for convenience. Application may be by low volume spray, to run-off, or otherwise as desired. Harvesting is then accomplished by exerting sufficient force on the fruit to remove it from the tree. Often, the weight of the fruit alone will cause it to fall from the tree, demonstrating a pull force of less than 0.5 kg. More typically, some positive force must be applied, such as mechanical shaking or from air or water guns.

In order that those skilled in the art may more readily understand the present invention and certain preferred embodiments by which it may be carried into effect, the following specific examples are afforded.

EXAMPLE 1

The ability of the present invention to increase internal ethylene production on external application to fruit is demonstrated by this Example. Acetone solutions of 5-chloro-3-methyl-4-nitro-1H-pyrazole (pyrazole) and the various compounds are prepared in concentrations such that 1 ml contains the amount of active ingredient(s) set forth in the following Table I. Hamlin oranges are then selected for uniformity of size, color, and shape and freedom from imperfections. These oranges are sprayed with 1 ml of the solution in question, loosely covered with clear plastic, and placed in a growth chamber maintained at 24° C daytime and 16° C nighttime with a light intensity of 800 $\mu E/m^2$/sec. At the indicated intervals a syringe is employed to extract a gas sample from inside the orange near the stem area, which sample is then analyzed for ethylene by gas chromatography on an instrument sensitive to the 10 ppb level. Each result reported is the average of three replicated tests.

TABLE I

| Pyrazole (μg/fruit) | Compound | (μg/fruit) | Internal 3 day (ppm/ml) | $C_2H_4$ 7 day (ppm/ml) |
|---|---|---|---|---|
| 0 | — | 0 | 0.11 | 0.08 |
| 50 | — | 0 | 2.32 | 1.11 |
| 100 | — | 0 | 3.48 | 1.66 |
| 0 | N-[(trichloromethyl)thio] phthalimide | 50 | 0.18 | 0.12 |
| 0 | " | 250 | 0.20 | 0.13 |
| 50 | " | 50 | 2.50 | 1.15 |
| 50 | " | 250 | 3.64 | 1.63 |
| 0 | N-[(trichloromethyl)thio]-4-cyclo- | 50 | 0.18 | 0.09 |
| 0 | hexene-1,2-dicarboximide | 250 | 0.18 | 0.10 |
| 50 | " | 50 | 2.44 | 1.26 |
| 50 | " | 250 | 3.15 | 1.83 |
| 0 | N-[(1,1,2,2-tetrachloroethyl)thio]- | 50 | 0.20 | 0.12 |
| 0 | 4-cyclohexene-1,2-dicarboximide | 250 | 0.21 | 0.20 |
| 50 | " | 50 | 2.20 | 1.06 |

TABLE I-continued

| Pyrazole (μg/fruit) | Compound | (μg/fruit) | Internal 3 day (ppm/ml) | $C_2H_4$ 7 day (ppm/ml) |
| --- | --- | --- | --- | --- |
| 50 | " | 250 | 4.37 | 1.92 |
| 0 | ferric dimethyldithiocarbamate | 50 | 0.19 | 0.14 |
| 0 | " | 250 | 0.16 | 0.18 |
| 50 | " | 50 | 2.54 | 1.43 |
| 50 | " | 250 | 4.01 | 2.37 |
| 0 | ethylenebisdithiocarbamate Mn | 50 | 0.18 | 0.15 |
| 0 | " | 250 | 0.14 | 0.11 |
| 50 | " | 50 | 2.24 | 1.10 |
| 50 | " | 250 | 2.96 | 1.18 |
| 0 | ethylenebisdithiocarbamate Zn | 50 | 0.17 | 0.10 |
| 0 | " | 250 | 0.14 | 0.09 |
| 50 | " | 50 | 2.58 | 1.82 |
| 50 | " | 250 | 2.64 | 2.03 |
| 0 | methyl-1-(butylcarbamoyl)-2-benzimidazolecarbamate | 50 | 0.15 | 0.06 |
| 0 | " | 250 | 0.13 | 0.15 |
| 50 | " | 50 | 2.41 | 1.53 |
| 50 | " | 250 | 5.05 | 1.82 |
| 0 | tetrachloroisophthalonitrile | 50 | 0.18 | 0.19 |
| 0 | " | 250 | 0.16 | 0.14 |
| 50 | " | 50 | 4.16 | 3.27 |
| 50 | " | 250 | 5.27 | 1.40 |

From Table I the increase in internal ethylene production over the pyrazole alone is readily apparent. This occurs even though none of the added compounds themselves has any significant effect on ethylene production.

EXAMPLE 2

Table II demonstrates the utility of the present invention on growing Valencia oranges. In each instance, a branch of a Valencia orange tree, bearing from 20 to 30 mature fruit, is treated to run-off with aqueous formulations containing the concentrations of active ingredients indicated in the table. Seven days after application of the formulation, the force necessary to remove the fruit from the stems is measured, with the results shown in the following table. Each result is an average of 3 replicate treatments.

TABLE II

| Pyrazole (ppm) | TCIPN[1] (ppm) | Removal Force (kg) | Reduction[2] (%) |
| --- | --- | --- | --- |
| 0 | 0 | 7.7 | — |
| 0 | 500,750,1000 | 7.7 | — |
| 150 | 0 | 7.7 | — |
| 150 | 500 | 5.4 | 30 |
| 150 | 750 | 4.8 | 38 |
| 150 | 1000 | 4.4 | 43 |
| 200 | 0 | 7.7 | — |
| 200 | 500 | 4.5 | 42 |
| 200 | 750 | 3.9 | 49 |
| 200 | 1000 | 3.7 | 52 |
| 250 | 0 | 6.0 | — |
| 250 | 500 | 4.2 | 30 |
| 250 | 750 | 3.7 | 38 |
| 250 | 1000 | 2.7 | 55 |
| 300 | 0 | 4.7 | — |
| 300 | 500 | 2.6 | 45 |
| 300 | 750 | <0.5 | >89 |
| 300 | 1000 | <0.5 | >89 |

[1]Tetrachloroisophthalonitrile
[2]Over abscission agent alone

In addition to demonstrating the synergistic effect obtainable by combining one of the additive compounds with the pyrazole, the table also demonstrates the correlation between the ability of a compound to increase the ethylene producing capacity of an abscission agent and the resultant beneficial effect when employed on fruit.

EXAMPLE 3

In a further field test, aqueous formulations containing in the first instance 400 ppm of 5-chloro-3-methyl-4-nitro-1H-pyrazole and in the second instance 250 ppm of the pyrazole and 1000 ppm of tetrachloroisophthalonitrile are applied to an entire tree bearing mature Valencia oranges. Seven days later, the fruits are harvested, employing an air-powered mechanical harvester. Five trees treated with the pyrazole alone show an average of 89.3% fruit harvested while the combination of ingredients, again on a five tree average, shows a harvest of 94.5%. The ability to reduce the amount of the abscission agent employed while still obtaining an improved result is clearly shown.

I claim:

1. A composition capable of promoting fruit abscission which composition consists essentially of 5-chloro-3-methyl-4-nitro-1H-pyrazole and tetrachloroisophthalonitrile wherein the amount of said 5-chloro-3-methyl-4-nitro-1H-pyrazole in said composition is not in excess of about 300 ppm.

2. A composition as in claim 1 wherein the ratio of tetrachloroisophthalonitrile to the pyrazole is 1 to 5:1.

3. A method of harvesting mature fruit from a tree which method comprises applying to the fruit locus an abscission-promoting amount of a composition consisting essentially of 5-chloro-3-methyl-4-nitro-1H-pyrazole in an amount not in excess of about 300 ppm and tetrachloroisophthalonitrile and, subsequently, exerting sufficient force on said fruit to remove same.

4. A method as in claim 3 wherein the ratio of the tetrachloroiso-phthalonitrile to the pyrazole is 1 to 5:1.

5. A method as in claim 3 wherein application is to run-off of a formulation containing about 300 ppm of said pyrazole and about 1000 ppm of said tetrachloroisophthalonitrile.

* * * * *